United States Patent
Qi et al.

(10) Patent No.: US 11,820,740 B1
(45) Date of Patent: Nov. 21, 2023

(54) OLEFIN METATHESIS BY REACTIVE DISTILLATION

(71) Applicant: Chevron Phillips Chemical Company LP, The Woodlands, TX (US)

(72) Inventors: Wei Qi, Kingwood, TX (US); Enrique Mancillas, Houston, TX (US); Jeffery C Gee, Kingwood, TX (US); Sean K. McLaughlin, Houston, TX (US); Jared Fern, Kingwood, TX (US); Steven Bischof, Spring, TX (US); Paul Hobson, Humble, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 17/821,375

(22) Filed: Aug. 22, 2022

(51) Int. Cl.
| | |
|---|---|
| *C07C 4/06* | (2006.01) |
| *C07C 6/04* | (2006.01) |
| *C07C 7/148* | (2006.01) |
| *B01D 3/26* | (2006.01) |
| *B01D 3/00* | (2006.01) |
| *C07C 7/04* | (2006.01) |
| *B01D 3/32* | (2006.01) |

(52) U.S. Cl.
CPC .............. *C07C 6/04* (2013.01); *B01D 3/009* (2013.01); *B01D 3/26* (2013.01); *C07C 7/04* (2013.01); *C07C 7/14883* (2013.01); *B01D 3/322* (2013.01)

(58) Field of Classification Search
CPC ......... C07C 6/04; C07C 7/04; C07C 7/14883; B01D 3/009; B01D 3/26; B01D 3/322
See application file for complete search history.

(56) References Cited

U.S. PATENT DOCUMENTS

| | | | |
|---|---|---|---|
| 6,646,172 B1 * | 11/2003 | Schwab | ............ C07C 6/04 585/315 |
| 7,220,886 B2 | 5/2007 | Podrebarac | |
| 8,455,416 B2 | 6/2013 | Bagheri | |
| 8,765,984 B2 | 7/2014 | Upshaw | |
| 9,611,193 B2 | 4/2017 | Choi | |
| 10,543,475 B2 | 1/2020 | Xu | |
| 10,814,301 B2 | 10/2020 | Xu | |
| 10,814,302 B2 | 10/2020 | Yongqiang | |
| 2003/0135080 A1 | 7/2003 | Botha | |
| 2006/0089517 A1 | 4/2006 | Podrebarac | |
| 2008/0103346 A1 | 5/2008 | Burdett | |
| 2008/0146856 A1 | 6/2008 | Leyshon | |

OTHER PUBLICATIONS

"Novel Catalytic Reactive Distillation Processes for a Sustainable Chemical Industry" Anton Kiss, Topics in Catalysis, pp. 1132-1148 (Year: 2018).*

(Continued)

*Primary Examiner* — Thuan D Dang
(74) *Attorney, Agent, or Firm* — Scheef & Stone, LLP

(57) ABSTRACT

Processes and reaction systems for olefin metathesis by reactive distillation, utilizing liquid phase metathesis of reactant olefins in the presence of a homogeneous metathesis catalyst system, where the light metathesis product is produced and leaves the liquid phase as vapor phase and the heavy metathesis product is produced in liquid phase. Separation can be performed on the light metathesis product and a distinct other separation can be performed on the heavy metathesis product.

20 Claims, 2 Drawing Sheets

(56) References Cited

OTHER PUBLICATIONS

Al-Arfaj, et al., Design and control of an olefin metathesis reactive distillation column. Chemical Engineering Science, 2002, 57(5), 715-733.

Morrison, et al., "Olefin Production Via Reactive Distillation Based Olefin Metathesis"; Paper 76d, Advances in Distillation & Absorption I, Separations Division, AIChE Annual Meeting, 2010.

* cited by examiner

OLEFIN METATHESIS BY REACTIVE DISTILLATION

FIELD OF THE DISCLOSURE

The present disclosure generally relates to metathesis reactions, and more particularly to the metathesis of olefins by reactive distillation.

BACKGROUND

Olefinic products can be produced by metathesis. Metathesis generally involves contacting one or more reactant olefins in the presence of a metathesis catalyst to form at least one olefinic product that is different from the one or more reactant olefins. Self-metathesis involves contacting one molecule of reactant olefin with a second molecule of the same reactant olefin to form one or more olefinic products that are different from the reactant olefin. Cross-metathesis involves contacting a molecule of a first reactant olefin with a molecule of a second reactant olefin to form one or more olefinic products different from the reactant olefins.

In the batch metathesis of linear olefins that produces a light olefin product (e.g., ethylene and/or propylene), the light olefin product can accumulate in the reactor and form products other than the target olefin products. One solution to remove the light olefin product in batch mode is to operate the reactor under a vacuum pressure; however, vacuum pressure can have low separation efficiency and can be cost-prohibitive in large scale operations.

There is a need for a metathesis process than can be performed on a large scale and in which the light olefin product can be removed from reaction to reduce the formation of undesired byproducts that are not the target olefin products.

SUMMARY

A process for olefin metathesis by reactive distillation can include reacting, in a reaction zone, a first reactant olefin in a presence of a homogeneous metathesis catalyst system to form a metathesis product comprising a first product olefin (a light product olefin) and a second product olefin (a heavy product olefin). Metathesis that is accomplished by the process can be performed on a continuous, as opposed to batch, basis. The first product olefin (e.g., the light product olefin) can be removed from the reaction zone on a continuous basis to reduce and/or prevent the formation of byproducts that are not the target product olefins.

The process can take place in a distillation column having the reaction zone, a first product separation zone, and a second product separation zone. The reaction zone can include a liquid collection tray and can be positioned above a first product separation zone and below the second product separation zone. The process can additionally include separating, in the first product separation zone, unreacted reactant olefin and second product olefin in liquid phase into a vapor portion containing the unreacted reactant olefin and a liquid portion containing the second product olefin, where the vapor portion is recycled to the reaction zone via a vapor passage in the liquid collection tray. The process can also include separating, in the second product separation zone, unreacted reactant olefin and first product olefin in vapor phase into a vapor portion containing the first product olefin and a liquid portion containing the unreacted reactant olefin, wherein the liquid portion is recycled to the reaction zone.

The process can alternatively take place in a distillation column having the reaction zone and the second product separation zone, and in a stripping column configured as the first product separation zone. The reaction zone comprises or consists of the liquid phase and is below the second product separation zone in the distillation column. The process can include separating, in the stripping column of the first product separation zone, unreacted reactant olefin and second product olefin received as a top reflux into a vapor portion containing the unreacted reactant olefin and a liquid portion containing the second product olefin, where the vapor portion is recycled to the reaction zone via a stream that is fluidly connected to a top of the stripping column and to the reaction zone of the distillation column. The process can also include separating, in the second product separation zone that is in the distillation column above the reaction zone, unreacted reactant olefin and first product olefin in vapor phase into a vapor portion containing the first product olefin and a liquid portion containing the unreacted reactant olefin, wherein the liquid portion is recycled to the reaction zone.

An olefin metathesis system comprising: a distillation column having a reaction zone, a first product separation zone below the reaction zone, and a second product separation zone above the reaction zone, wherein the reaction zone is configured to contact a first reactant olefin in the presence of a homogeneous metathesis catalyst system to form a metathesis product comprising a first product olefin and a second product olefin, wherein the reaction zone has a reactive tray and a liquid collection tray below the reactive tray, wherein the first product separation zone has at least one distillation structure, wherein the first product separation zone is fluidly connected to the reaction zone via a vapor passage of the liquid collection tray; a catalyst removal unit fluidly connected to the liquid collection tray of the reaction zone of the distillation column and configured to receive a liquid phase containing the second product olefin, unreacted reactant olefin, and the homogeneous metathesis catalyst system from the liquid collection tray and to separate the liquid phase into a first stream comprising the unreacted reactant olefin and the second product olefin and a second stream comprising the homogeneous metathesis catalyst system; wherein the first stream is connected to the catalyst removal unit and to the first product separation zone of the distillation column, and wherein the first product separation zone is configured to separate the unreacted reactant olefin and the second product olefin into vapor portion containing the unreacted reactant olefin and a liquid portion containing the second product olefin. The system can perform metathesis on a continuous basis.

An olefin metathesis system comprising: a distillation column having a reaction zone and a product separation zone above the reaction zone, wherein the reaction zone is configured to contact a first reactant olefin in the presence of a homogeneous metathesis catalyst system to form a metathesis product comprising a first product olefin and a second product olefin, wherein the reaction zone has a reactive tray and a liquid collection tray below the reactive tray, wherein the product separation zone has at least one distillation structure, wherein the product separation zone is configured to receive a vapor phase containing unreacted reactant olefin and first product olefin from the reaction zone; a catalyst removal unit fluidly connected to reaction zone of the distillation column and configured to receive a liquid phase containing the second product olefin, unreacted reactant olefin, and the homogeneous metathesis catalyst system from the reaction zone of the distillation column and to separate the liquid phase into a first stream comprising the unreacted reactant olefin and the second product olefin and a second stream comprising the homogeneous metathesis catalyst system; a stripping column fluidly connected to the first stream and configured to receive the first stream at a top of the stripping column as reflux and to separate the first stream into a vapor portion comprising the unreacted reactant olefin and a liquid portion comprising the second product olefin, wherein the product separation zone is configured to separate the unreacted reactant olefin and the first product olefin into vapor portion containing the first product olefin and a liquid portion containing the unreacted reactant olefin. The system can perform metathesis on a continuous basis.

Other technical features may be readily apparent to one skilled in the art from the following figures, descriptions and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

Figure 1A:
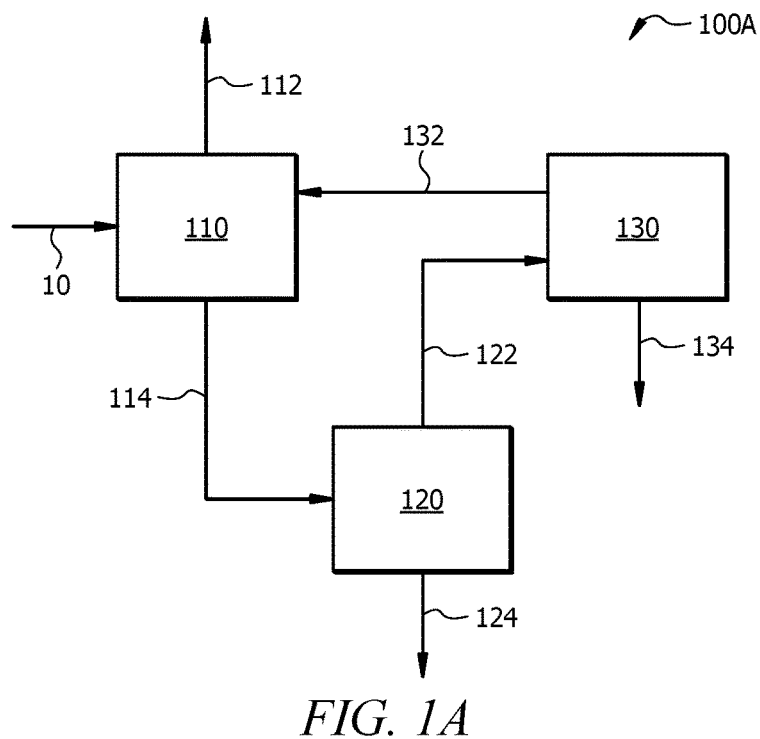
FIG. 1A illustrates a schematic diagram of a metathesis reaction process.

Illustrative aspects of the subject matter claimed herein will now be disclosed. In the interest of clarity, not all features of an actual implementation are described in this specification. It can be appreciated that in the development of any such actual aspect, numerous implementation-specific decisions must be made to achieve the developers' specific goals, such as compliance with system-related and business-related constraints, which can vary from one implementation to another. Moreover, it can be appreciated that such a development effort, even if complex and time-consuming, would be a routine undertaking for those of ordinary skill in the art having the benefit of this disclosure.

Unless otherwise specified, the terms "contact" and "combine," and their derivatives, can refer to any addition sequence, order, or concentration for contacting or combining two or more components of the disclosed embodiments.

The term "stream" as used herein refers to a composition of the components disclosed herein for the respective stream. The term "stream" can additionally refer to and imply associated equipment, such as conduit, line, and pipe that is used to move the composition from one location to another (e.g., a stream from one equipment unit to another equipment unit). Alternatively, the term "stream" refers only to the composition contained within the equipment (e.g., a stream moving from one zone to another zone where both zones are contained within the same equipment unit).

The term "olefin" whenever used in this specification and claims refers to hydrocarbons that have at least one carbon-carbon double bond that is not part of an aromatic ring or an aromatic ring system. The term "olefin" includes aliphatic and aromatic, cyclic and acyclic, and/or linear and branched hydrocarbons having at least one carbon-carbon double bond that is not part of an aromatic ring or ring system unless specifically stated otherwise. Olefins having only one, only two, only three, etc., carbon-carbon double bonds can be identified by use of the term "mono," "di," "tri," etc., within the name of the olefin. The olefins can be further identified by the position of the carbon-carbon double bond(s).

The term "alpha olefin" as used in this specification and claims refers to an olefin that has a carbon-carbon double bond between the first and second carbon atoms of the longest contiguous chain of carbon atoms. The term "alpha olefin" includes linear and branched alpha olefins unless expressly stated otherwise. In the case of branched alpha olefins, a branch can be at the 2-position (a vinylidene) and/or the 3-position or higher with respect to the olefin double bond. The term "vinylidene" whenever used in this specification and claims refers to an alpha olefin having a branch at the 2-position with respect to the olefin double bond. By itself, the term "alpha olefin" does not indicate the presence or absence of other carbon-carbon double bonds unless explicitly indicated.

The term "normal alpha olefin" whenever used in this specification and claims refers to a linear aliphatic mono-olefin having a carbon-carbon double bond between the first and second carbon atoms. It is noted that "normal alpha olefin" is not synonymous with "linear alpha olefin" as the term "linear alpha olefin" can additionally include linear olefinic compounds having a double bond between the first and second carbon atoms and additional double bonds.

Terms that refer to a state of matter, such as solid, liquid, liquid portion, gas, vapor, vapor portion, solid phase, liquid phase, gas phase, and vapor phase, refer to the state of matters under the operating conditions in the respective step of the disclosed processes. For example, "liquid phase" in context of i) the reaction zone disclosed herein refers to a liquid being present at the temperature and pressure at which the metathesis reaction occurs in the reaction zone, ii) streams, lines, conduits that exist between the reaction zone and the catalyst separation zone refers to a liquid being present at the temperature and pressure in said streams, lines, and conduits iii) the catalyst separation zone refers to a liquid being present at the temperature and pressure at which the separations take place. Similarly, "vapor phase" in context of the reaction zone disclosed herein refers to a gas or vapor being present at the temperature and pressure at which the metathesis reaction occurs in the reaction zone.

Disclosed herein are processes and apparatuses for metathesis of olefins by reactive distillation. The metathesis reaction occurs in the liquid phase with a homogeneous metathesis catalyst system also in the liquid phase. The reactions occur under conditions by which the light product olefin (e.g., ethylene, propylene, or both ethylene and propylene) that is produced by the metathesis reaction is in a vapor phase, separates from the liquid phase as vapor, and does not further react with the homogeneous metathesis catalyst system that is in the liquid phase—thus reducing the formation of undesired byproducts. The process is generally operated on a continuous basis.

Figure 1B:
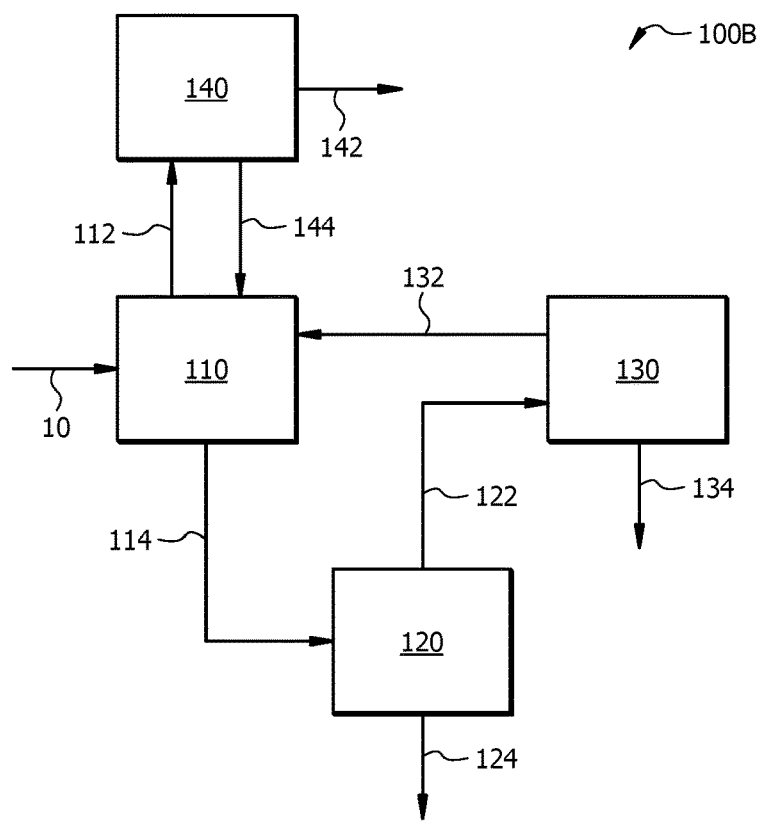
FIG. 1B illustrates a schematic diagram of another metathesis reaction process.

FIGS. 1A and 1B illustrate schematic diagrams of metathesis reaction processes 100A and 100B. Steps of the processes 100A and 100B take place in a reaction zone 110, a catalyst separation zone 120, and a product separation zone 130. Additional steps of process 100B can take place in a second product separation zone 140.

The processes 100A and 100B generally begin with introducing reaction components to the reaction zone 110. The reaction components include one reactant olefin (a reactant olefin) or two reactant olefins (a first reactant olefin and a second reactant olefin). Use of "reactant olefin(s)" herein is intended to include both of these aspects and embodiments. Thus, in some aspects the processes 100A and 100B can include introducing a first reactant olefin to the reaction zone 110; and other aspects can include introducing a first reactant olefin and a second reactant olefin to the reaction zone 110. Introducing the reaction components can occur on a continuous basis.

Reactant olefin(s) can be introduced to the reaction zone 110 via feed stream 10. In some aspects, the reactant olefin includes one olefin; alternatively, the reactant olefins include two olefins; alternatively, the reactant olefin(s) can include three or more olefins. When two different reactant olefins are employed, the molar ratio of a first reactant olefin to a second reactant olefin can be in a range of from about 0.8:1 to about 1.2:1. For example, the molar ratio of a first reactant olefin to a second reactant olefin can be 1:1. When two different reactant olefins are employed, the first reactant olefin and the second reactant olefin can be introduced to the reaction zone 110 via feed stream 10; alternatively, the first reactant olefin can be introduced to the reaction zone 110 via feed stream 10 and the second reactant olefin can be introduced to the reaction zone 110 via a separate stream that is fluidly connected to the reaction zone 110.

One or more of the reactant olefin(s) in the feed stream 10 can be selected from any olefin having 1, 2, 3, 4, 5, 6, 7, 8, 9, 10, 11, 12, 13, 14, 15, 16, 17, 18, 19, or 20 carbon atoms; additionally or alternatively, one or more reactant olefin(s) in the feed stream 10 can be selected from any olefin that is an alpha olefin; additionally or alternatively, one or more reactant olefin(s) in the feed stream 10 can be selected from an olefin that is a normal alpha olefin. Specific nonlimiting examples of reactant olefin(s) can include, but are not limited to, 1-butene, 1-pentene, 1-hexene, 1-heptene, 1-octene, 1-nonene, 1-decene, 1-undene, 1-dodecene, 1-tridecene, 1-tetradecene, 1-butene in combination with a higher carbon number olefin, or 1-hexene in combination with a higher carbon number olefin, or combinations thereof.

In additional aspects, the processes 100A and 100B can include introducing the homogeneous metathesis catalyst system to the reaction zone 110. In some aspects, the homogeneous metathesis catalyst system can be introduced via stream 10, while in other aspects the homogeneous metathesis catalyst system is introduced in a stream that is separate and different than stream 10. For example, the homogeneous metathesis catalyst system can be contained in a catalyst stream that combines with a reactant stream containing the reactant olefin(s) to form the feed stream 10 that introduces the reactant olefin(s) and the homogeneous metathesis catalyst system to the reaction zone 110. Alternatively, the homogeneous metathesis catalyst system can be contained in a catalyst stream that feeds the homogeneous metathesis catalyst system to the reaction zone 110 separately from the reactant olefin(s) in the feed stream 10.

Any suitable homogeneous metathesis catalyst system can be used. The homogeneous metathesis catalyst system generally includes a metathesis catalyst dissolved in an inert solvent, such as toluene. Non-limiting examples of the homogeneous metathesis catalyst system can include a metal oxide based metathesis catalyst system, a metal halide based metathesis catalyst system, a metal carbene based metathesis catalyst system (also referred to as a Grubbs catalyst based catalyst system), or any combination thereof. In one aspect, the metathesis catalyst system can be a metal oxide based metathesis catalyst system or a metal halide based metathesis catalyst system; alternatively, a metal oxide based metathesis catalyst system; alternatively, a metal halide based metathesis catalyst system; or alternatively, a metal carbene based metathesis catalyst system.

Metal oxide based metathesis catalyst systems can comprise (or consist essentially of, or consist of) cobalt oxide, molybdenum oxide, tungsten oxide, rhenium oxide, or any combination thereof. For instance, the metal oxide based catalyst system can comprise (or consist essentially of, or consist of) cobalt oxide; alternatively, molybdenum oxide; alternatively, tungsten oxide; or alternatively, rhenium oxide. Optionally, the metal oxide based metathesis catalyst system can further comprise a support, or a metal alkyl activator, or both a support and a metal alkyl activator. Illustrative supports can include alumina, silica, silica-alumina, and aluminum-phosphate, amongst other solid oxide materials. Accordingly, non-limiting examples of supported metal oxide based metathesis catalyst systems can include molybdenum oxide on alumina ($MoO_3/Al_2O_3$), tungsten oxide on silica ($WO_3/SiO_2$), rhenium oxide on alumina ($Re_2O_7/Al_2O_3$), cobalt oxide and molybdenum oxide on alumina ($CoO/MoO_3/Al_2O_3$), or rhenium oxide on alumina activated with tetramethyl tin ($Re_2O_7/Al_2O_3/SnMe_4$). Other suitable metal oxide based metathesis catalyst systems are known to those skilled in the art.

The metal oxide based metathesis catalyst system can further include a metal alkyl activator. In an aspect, the metal alkyl can comprise, can consist essentially of, or can be an alkyl lithium, an alkyl magnesium, an alkyl aluminum, alkyl tin compounds, or any mixture thereof. In an aspect, the metal alkyl activator can be an alkyl lithium compound. In another aspect, the metal alkyl activator can comprise, can consist essentially of, or can be an alkyl magnesium compound; alternately an alkyl aluminum compound; or alternatively, an alkyl tin compound. Non-limiting examples of alkyl aluminum compounds can include trialkyl aluminum compounds and/or alkyl aluminum halide compounds. The alkyl groups on the metal alkyl activator can include any C1 to C10 hydrocarbyl group, or alternatively, any C1 to C5 hydrocarbyl group. In various embodiments, the alkyl group for the metal alkyl activator can be a methyl group, ethyl group, n-propyl group, iso-propyl group, n-butyl group, sec-butyl group, or tert-butyl group; alternatively, a methyl group, ethyl group, n-butyl group, sec-butyl group, or tert-butyl group; alternatively, a methyl group; alternatively, an ethyl group; alternatively, an n-butyl group; alternatively, a sec-butyl group; or alternatively, a tert-butyl group. Representative examples of suitable trialkyl aluminum compounds can include trimethylaluminum, triethylaluminum, triisobutylaluminum, or combinations thereof. The halide of the alkyl aluminum halide compound can be chloride, bromide, or iodide; alternatively, chloride; alternatively, bromide; or alternatively, iodide. Examples of suitable alkyl aluminum halide compounds can include ethylaluminum dichloride, diethylaluminum chloride, ethylaluminum sesquichloride, or combinations thereof. Suitable and non-limiting examples of alkyl tin compounds can include tetramethyl tin, tetraethyl tin, tetrabutyl tin, or combinations thereof.

Metal halide based metathesis catalyst systems can comprise (or consist essentially of, or consist of) a halide of tungsten, a halide of molybdenum, or a combination thereof. For instance, the metal halide based metathesis catalyst system can comprise (or consist essentially of, or consist of) a halide of tungsten; or alternatively, a halide of molybdenum. The halide of the metal halide based metathesis catalyst system can be chloride, bromide, or iodide. In an aspect, the halide can comprise, consist essentially of, or can be, chloride; alternatively, bromide; or alternatively, iodide. Hence, the metal halide based metathesis catalyst system can comprise (or consist essentially of, or consist of) tungsten chloride, molybdenum chloride, or a mixture thereof; alternatively, tungsten chloride; or alternatively, molybdenum chloride.

Optionally, the metal halide based metathesis catalyst system can further comprise a metal alkyl activator (as described herein), oxygen, an alcohol, or any combination thereof; alternatively, a metal alkyl activator; alternatively, oxygen; or alternatively, an alcohol. Non-limiting examples of metal halide based metathesis catalyst systems can include tungsten chloride/tetrabutyl tin ($WCl_6/SnMe_4$), tungsten chloride/ethylaluminum dichloride ($WCl_6/EtAlCl_2$), tungsten chloride/ethylaluminum dichloride/ethyl alcohol ($WCl_6/EtAlCl_2/EtOH$), molybdenum chloride/triethyl aluminum ($MoCl_5/AlEt_3$), or molybdenum chloride/triethyl aluminum/$O_2$ ($MoCl_5/AlEt_3/O_2$). Other suitable metal halide based metathesis catalyst systems are known to those skilled in the art.

The metal of the metal carbene based metathesis catalyst systems can comprise (or consist essentially of, or consist of) tungsten, tantalum, osmium, molybdenum, ruthenium, or any combination thereof. For instance, the metal of the metal carbene based metathesis catalyst system can comprise (or consist essentially of, or consist of) tungsten; alternatively, tantalum; alternatively, osmium; alternatively, molybdenum; or alternatively, ruthenium. These metal carbene based metathesis catalyst systems can contain compounds which have a stable metal-carbon double bond or can form a metal-carbon double bond in situ from a metal precursor having a stable metal-carbon single bond.

The processes 100A and 100B can include reacting, in the reaction zone 110, the first reactant olefin in a presence of the homogeneous metathesis catalyst system to from the metathesis product containing a first product olefin and a second product olefin.

The reaction zone 110 disclosed herein is defined as an area in a metathesis reaction apparatus having any configuration of equipment (e.g., vessel(s), piping, valve(s), combinations thereof) suitable for metathesis reactions to occur as disclosed herein, where all the necessary reaction components (e.g., reactant olefin(s) and homogeneous metathesis catalyst system) and reaction conditions (e.g., temperature, pressure, flow rate, reactant olefin concentration) are present such that the metathesis reaction can occur at a desired rate. In some aspects, the boundary of the reaction zone 110 can be defined by the necessary reaction components and reaction conditions being present to maintain the metathesis reaction within 25 percent of the average reaction rate (e.g., based upon a volume average of the reaction rate of the reaction zone 110). In aspects, the reaction zone 110 can be embodied as at least a portion of a distillation column or other vessel configured to hold a liquid phase in which reaction phase takes place while allowing vapor phase to escape into a space in the column or vessel that is above the liquid phase.

In aspects, the reaction zone 110 does not include a heterogeneous metathesis catalyst or a heterogeneous metathesis catalyst system. That is, embodiments contemplate that the metathesis catalyst remains dissolved in liquid while in the reaction zone 110.

Contacting the reactant olefin(s) in the presence of the homogeneous metathesis catalyst system in the reaction zone 110 (in liquid phase) converts at least a portion of the total amount of reactant olefin(s) in the reaction zone 110 to metathesis product. The metathesis product can contain a first product olefin (e.g., the light metathesis product, for example, ethylene or propylene) and a second olefin (e.g., the heavy metathesis product). Other olefin products can also be produced in amounts smaller than the amounts produced for the first product olefin and the second product olefin.

The operating conditions of the reaction zone 110 are configured such that the first product olefin is present in a vapor phase that separates from the liquid phase in which the metathesis reaction occurs. In aspects, a first concentration of the first product olefin in the liquid phase is less than a second concentration of the first product olefin in the vapor phase. In aspects, the concentration of the first product olefin (e.g., ethylene) in the liquid phase can be less than about 1, 0.9, 0.8, 0.7, 0.6, 0.5, 0.4, 0.3, 0.2, or 0.02 wt % based on a total weight of the first product olefin in the liquid phase. In embodiments, the concentration of the first product olefin (e.g., ethylene) in the vapor phase can be in a range of from about 1 mol % to about 9 mol %; alternatively, from about 2 mol % to about 8 mol % based on a total moles of the vapor phase. For example, in aspects involving self-metathesis of 1-hexene, the concentration of ethylene in the vapor phase can be about 3.5 mol %. In another example for aspects involving self-metathesis of 1-butene, the concentration of the ethylene in the vapor phase can be about 7.0 mol %.

Any conditions capable of forming a metathesis product having a first product olefin in vapor phase and one or more reactant olefins in liquid phase can be utilized, for example process conditions as set forth in U.S. Patent Application Publication No. 2003/0135080 and U.S. Pat. No. 8,765,984. Metathesis conditions capable of forming a metathesis product can include, but are not limited to, pressure, temperature, time, and concentration (in relations to solution phase formation of the metathesis product) and are independently described herein. These independently described conditions can be utilized in any combination and without limitation, to further described the process disclosed herein.

In aspects, the processes 100A and 100B can utilize any pressure capable of forming a metathesis product having a first product olefin in vapor phase and one or more reactant olefins in liquid phase. In an aspect, a minimum pressure which can be utilized to form the metathesis product (or the liquid metathesis product) can be 5 psia (34.5 kPa), 10 psia (68.9 kPa), 14 psia (96.5 kPa), 14.7 psia (101.4 kPa), 20 psia (138.9 kPa), or 50 psia (344.7 kPa); alternatively or additionally, a maximum pressure of 450 psia (3.1 MPa), 350 psia (2.4 MPa), 250 psia (1.7 MPa), or 150 psia (1.0 MPa). Ranges of pressure which can be utilized to form the metathesis product can range from any minimum pressure to any maximum pressure described herein for metathesis conditions. In some aspects, suitable ranges for the pressure which can be utilized to form the metathesis product (or the liquid metathesis product can include, but are not limited to, from 5 psia (34.5 kPa) to 450 psia (3.10 MPa); alternatively, from 10 psia (68.9 kPa) to 350 psia (2.4 MPa); alternatively, from 14 psia (96.5 kPa) to 250 psi (1.7 MPa); alternatively, from 14 psia (96.5 kPa) to 150 psia (1.0 MPa); alternatively, from 14.7 psia (101.4 kPa) to 150 psia (1.0 MPa); or alternatively, from 20 psia (138.9 kPa) to 150 psia (1.0 MPa). Other pressure ranges which can be utilized to form the metathesis product are readily apparent to those skilled in the art with the aid of this disclosure.

In aspects, the processes 100A and 100B can utilize any temperature capable of forming a metathesis product having a first product olefin in vapor phase and one or more reactant olefins in liquid phase. In an aspect, the minimum temperature which can be utilized to form the metathesis product can be 30° C., 35° C., 40° C., 45° C., or 50° C.; alternatively or additionally, the maximum temperature which can be utilized to form the metathesis product can be 150° C., 140° C., 130° C., 120° C., 110° C., 90° C., 80° C., 70° C., or 60° C. Ranges for the temperature which can be utilized to form the metathesis product can range from any minimum temperature described herein to any maximum temperature described herein. In some aspects, suitable ranges for the temperature which can be utilized to form the metathesis product can include, but are not limited to, from 30° C. to 150° C.; alternatively, from 35° C. to 100° C.; alternatively, from 40° C. to 90° C.; alternatively, from 45° C. to 80° C.; alternatively, from 50° C. to 70° C.; alternatively, from 50° C. to 65° C.; or alternatively, from 50° C. to 60° C. Other temperature ranges which can be utilized to form the metathesis product (or the liquid metathesis product) are readily apparent to those skilled in the art with the aid of this disclosure.

In aspects, the processes 100A and 100B can utilize any residence time in the reaction zone 110 (time period or average time period) necessary to form the desired quantity of metathesis product; alternatively, to provide a desired homogeneous metathesis catalyst system productivity; alternatively, to provide a desired conversion (e.g., at least 50 mass %, 60 mass %, 70 mass %, or 80 mass %). In an aspect, the minimum time (or minimum average time) which can be utilized to form the metathesis product can be 1 second, 1 minute, 2 minutes, 4 minutes, 6 minutes, 8 minutes, or 10 minutes; alternatively or additionally, maximum time (or average maximum time) can be 1 hour, 1.5 hours, 2 hours, 4 hours, 6 hours, 8 hours, or 10 hours. Ranges for the time (or average time) which can be utilized to form the metathesis product range from any minimum time to any maximum time described herein for metathesis conditions. In some aspects, suitable ranges for the time (or average time) which can be utilized to form the metathesis product can include, but are not limited to, from 1 second to 10 hours; alternatively, from 1 minute to 8 hours; alternatively, from 2 minutes to 6 hours; alternatively, from 4 minutes to 4 hours; alternatively, from 6 minutes to 2 hours; alternatively, from 8 minutes to 90 minutes; or alternatively, from 10 minutes to 1 hour. Other time (or average time) ranges which can be utilized to form the metathesis product (or the liquid metathesis product) are readily apparent to those skilled in the art with the aid of this disclosure.

In aspects, the processes 100A and 100B can form metathesis product using any concentration of the homogeneous metathesis catalyst system which can produce the desired quantity of metathesis product, desired metathesis catalyst system productivity, and/or desired conversion a reactant olefin(s) disclosed herein in the desired residence time (or average time). In an aspect, the minimum concentration for the homogeneous metathesis catalyst system can be 100, 200, 300, 400, or 500 ppm by mass; alternatively or additionally, the maximum concentration for the homogeneous metathesis catalyst system can be 1,000, 900, 800, 700, or 600 ppm by mass. Ranges of the concentration of the homogeneous metathesis catalyst system concentration which can be utilized can range from any minimum catalyst system concentration disclosed herein to any maximum catalyst system concentration disclosed herein. In some aspects, suitable ranges for the concentration for the homogeneous metathesis catalyst system which can be utilized to form the metathesis product can include, but are not limited to, 100 to 1,000 ppm, 110 to 900 ppm, 120 to 800 ppm, 130 to 700 ppm, or 130 ppm by mass. Other catalyst system concentration ranges which can be utilized to form the metathesis product are readily apparent to those skilled in the art with the aid of this disclosure. Generally, the ppm basis for the catalyst system concentration can be based upon the mass of the reactant olefin(s).

In aspects, the processes 100A and 100B can include removing metathesis product from the reaction zone 110. In embodiments, removing metathesis product from the reaction zone 110 can include removing the liquid phase containing the second product olefin (e.g., the heavy product olefin), the homogeneous metathesis catalyst system, and optionally unreacted reactant olefin from the reaction zone 110 and removing the vapor phase containing the first product olefin (e.g., the light product olefin) from the reaction zone 110. In aspects of these embodiments, the liquid phase and the vapor phase from the reaction zone 110 occurs on a continuous basis. In embodiments, the metathesis product olefin(s) can be removed from the reaction zone 110 via a first effluent stream 112 and a second effluent stream 114. The first product olefin and optionally unreacted reactant olefin, in vapor phase, can flow from the reaction zone 110 in stream 112. The second product olefin, in liquid phase, can flow from the reaction zone 110 in reaction zone effluent stream 114. The reaction zone effluent stream 114 can also contain the homogeneous metathesis catalyst system and any unreacted reactant olefin that is in the liquid phase.

The carbon number of the product olefin(s) produced in the reaction zone 110 depends on the reactant olefin(s) that are introduced to the reaction zone 110 and generally include the reaction product of the metathesis reaction that occurs by contact of the reactant olefin(s) in the presence of the homogeneous metathesis catalyst system in the reaction zone 110. In aspects, the first product olefin can have a carbon number that is less than a carbon number of the first reactant olefin, and the second product olefin can have a carbon number that is greater than the carbon number of the first reactant olefin. For example, self-metathesis of 1-butene as the reactant olefin in the presence of the homogeneous metathesis catalyst system can produce ethylene (the first product olefin) and 1-hexene (the second product olefin). In another example, self-metathesis of 1-hexene as the reactant olefin in the presence of the homogeneous metathesis catalyst system can produce ethylene (the first product olefin) and 1-decene (the second product olefin). In additional aspects for embodiments that include a second reactant olefin that is fed to the reaction zone 110, the first product olefin can have a carbon number that is less than a carbon number of both the first reactant olefin and the second reactant olefin, and the second product olefin can have a carbon number that is greater than the carbon number of the both the first reactant olefin and the second reactant olefin. For example, cross-metathesis of 1-butene and 1-tetradecene in the presence of the homogeneous metathesis catalyst system can product ethylene (the first product olefin) and a C16-olefin and/or a C26-olefin (either one can be the second product olefin).

The processes 100A and 100B can include introducing the liquid phase of the metathesis product that is in stream 114 into the catalyst separation zone 120, and separating the liquid phase into a first stream 122 containing the second product olefin and optionally the unreacted reactant olefin and a second stream 124 containing the homogeneous metathesis catalyst system. The homogeneous metathesis catalyst system in second stream 124 can be in the form of spent catalyst or can contain both spent and fresh catalyst.

The catalyst separation zone 120 disclosed herein generally includes any equipment configured to separate a mixture containing the product olefin(s) and the homogeneous metathesis catalyst system (e.g., in the form of spent catalyst or containing both spent and fresh catalyst) into a stream containing the homogeneous metathesis catalyst system and a stream containing the product olefin(s). The homogeneous metathesis catalyst system can be separated from the mixture by distillation (SPD), membrane separation, conversion of homogeneous catalyst to heterogeneous catalyst, phase separation, or solvent extraction. An example of membrane separation for separating a homogeneous metathesis catalyst from a metathesis reaction mixture is found in U.S. Patent Application Publication No. 2008/0103346.

In processes 100A and 100B, the mixture from which the homogeneous metathesis catalyst system is separated is received from stream 114, which contains the reaction effluent from the reaction zone 110.

The processes 100A and 100B can additionally include introducing the first effluent stream 112 into product separation zone 130, and separating, in the product separation zone 130, the second product olefin and the unreacted reactant olefin into a vapor portion containing the unreacted reactant olefin and a liquid portion containing the second olefin product. The vapor portion can be recovered in stream 132, and the liquid portion can be recovered in stream 134. In some aspects, the unreacted reactant olefin in vapor portion in stream 132 can be recycled to the reaction zone 110. In some aspects, the unreacted reactant olefin can be condensed (e.g., via a condenser in stream 132) and recycled to the reaction zone 110 in a liquid phase.

The process 100B of FIG. 1B additionally utilizes a second product separation zone 140. As described above, the first product olefin, in vapor phase, can flow from the reaction zone 110 in stream 112. Stream 112 can additionally include unreacted reactant olefin in the vapor phase. Thus, the second product separation zone 140 can be utilized for process 100B where the first effluent stream 112 contains the first product olefin and unreacted reactant olefin. Process 100B can additionally include introducing the vapor phase into the second product separation zone 140, and separating, in the second product separation zone 140, the vapor phase into a vapor portion containing the first product olefin and a liquid portion containing the unreacted reactant olefin. In these embodiments, a portion of the unreacted reactant olefin can be present in the vapor phase and another portion of the unreacted reactant olefin can be present in the liquid phase. In aspects, the vapor portion can flow from the second product separation zone 140 in stream 142, and the liquid portion can flow from the product separation zone 140 in stream 144 to the reaction zone 110.

Figure 2:
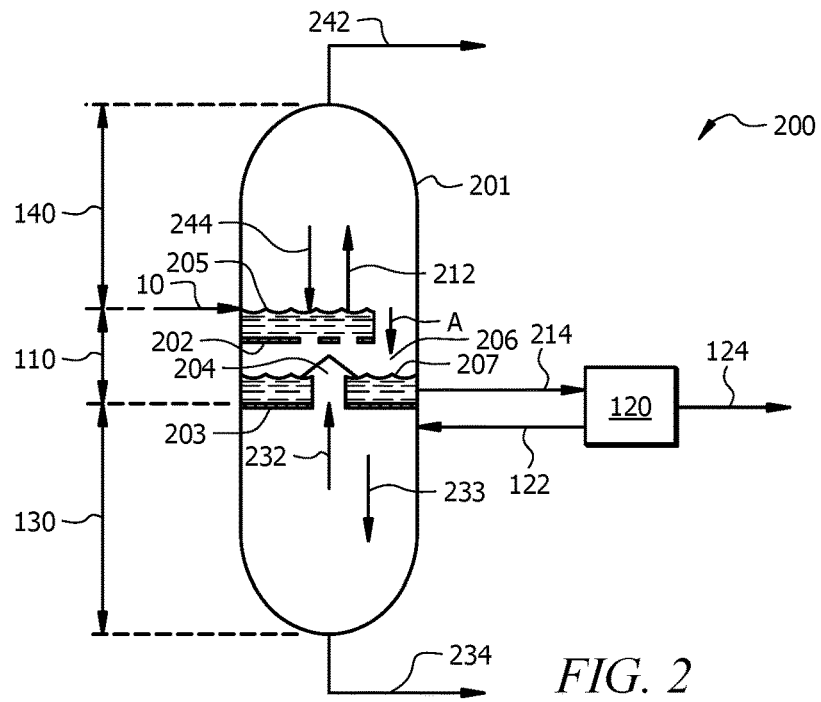
FIG. 2 illustrates a schematic diagram of an apparatus for performing an olefin metathesis process, where the reaction zone, first product separation zone, and second product separation zone are contained within a distillation column.
Figure 3:
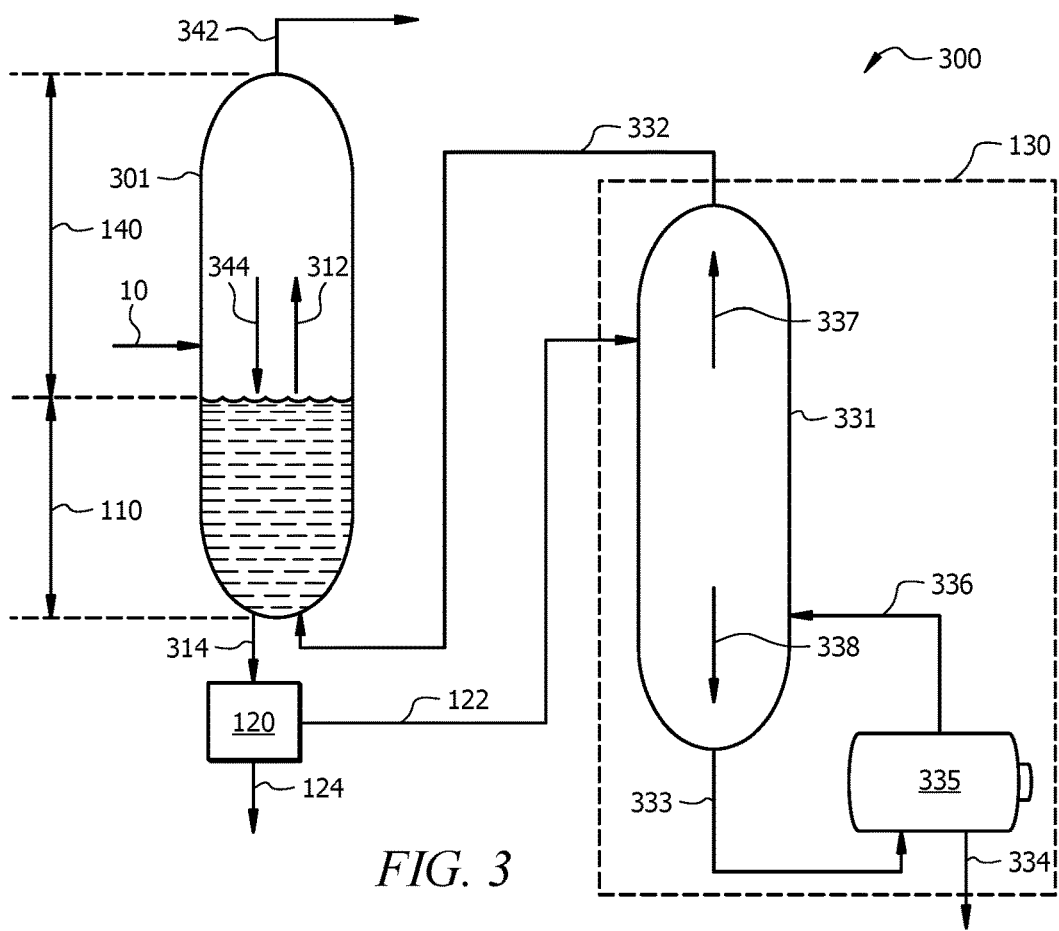
FIG. 3 illustrates a schematic diagram of another apparatus for performing an olefin metathesis process, where the reaction zone and the second product separation zone are contained within a distillation column and the first product separation zone includes a stripping column.

FIG. 2 and FIG. 3 illustrates apparatuses 200 and 300 that utilize the process 100B illustrated in FIG. 1B. The apparatuses 200 and 300 perform reactive distillation in a reaction zone 110 of a distillation column 201/301, followed by removal of spent catalyst, and then product olefin recovery. The liquid phase discussed hereinabove in both apparatuses 200 and 300 is contained within the reaction zone 110, and the distillation column 201 and 301 of each apparatus 200 and 300 is configured such that one or more reactant olefin(s) are introduced to the distillation column 201 and 301 and react in the presence of the homogeneous metathesis catalyst system in liquid phase in the reaction zone 110 to form the metathesis product comprising at least two product olefins (a first product olefin in vapor phase and a second product olefin in the liquid phase).

FIG. 2 illustrates a schematic diagram of an apparatus 200 for performing an olefin metathesis process, where the reaction zone 110, the first product separation zone 130, and the second product separation zone 140 are contained within the distillation column 201. The first product separation zone 130 is below the reaction zone 110, and the second product separation zone 140 is above the reaction zone 110. The second product separation zone 140 can also be referred to as a rectifying section of the distillation column 201.

The reaction zone 110 in the apparatus 200 has a liquid collection tray 203 positioned below a reactive tray 202 in the distillation column 201. The reactant olefin(s) and the homogeneous metathesis catalyst system are introduced via feed stream 10 into the distillation column 201 at a location that is above the reactive tray 202. The reactive tray 202 can be embodied as a sieve tray with a downcomer, for example. The liquid collection tray 203 can be embodied as a chimney tray, a vane collector tray, a trapout-pan, a flange-type collector tray, or combinations thereof. The liquid collection tray 203 may also be referred to as a bubble cap tray. The liquid collection tray 203 is generally configured with a vapor passage 204 through which the vapor portion of the product separation zone 130 can flow while the liquid phase in the reaction zone 110 does not flow in the vapor passage 204. The vapor passage 204 can be formed by one or more distillation tray chimneys, a vane configuration, or other structure or arrangement of structures that is/are configured to allow passage of vapor therethrough. Reaction components (e.g., the reactant olefin(s) and the homogeneous metathesis catalyst system) are introduced to the distillation column 201 above the reactive tray 202, and fall onto the reactive tray 202, creating a layer of liquid phase in the reaction zone 110 on the reactive tray 202. Liquid spills down (e.g., via a downcomer or a hole formed in the reactive tray 202) in the direction of arrow A to the liquid collection tray 203, creating another layer of liquid phase in the reaction zone 110 on the liquid collection tray 203.

As can be seen in FIG. 2, the liquid phase of the reaction zone 110 in the distillation column 201 is embodied as a first portion 205 of the liquid phase that is held up on the reactive tray 202 and a second portion 207 of the liquid phase that is held up on the liquid collection tray 203. The first portion 205 and the second portion 207 of the liquid phase are separated by a vapor space 206 that is between the top of the second portion 207 of the liquid phase and a bottom of the reactive tray 202. It is believed that no significant metathesis reaction occurs in the vapor space 206 of the reaction zone 110 of the distillation column 201, and the metathesis reaction occurs predominantly in the first portion 205 and second portion 207 of the liquid phase in the reaction zone 110.

Reaction effluent, also referred to herein as liquid phase, from the reaction zone 110 of apparatus 200 can flow in side draw stream 214 (stream 214 is equivalent of stream 114 in FIGS. 1A and 1B) to the catalyst separation zone 120. The side draw stream 214 is fluidly connected to the liquid collection tray 203 and to a catalyst separation unit of the catalyst separation zone 120. The catalyst separation unit in the catalyst separation zone 120 is configured, by a technique disclosed herein, to separate the liquid phase receive via stream 214 into a first stream 122 containing the second product olefin and any unreacted reactant olefin and a second stream 124 containing the homogeneous metathesis catalyst system. First stream 122 is fluidly connected to the catalyst separation unit in the catalyst separation zone 120 and to the product separation zone 130 in the distillation column 201.

The second product olefin and any unreacted reactant olefin are received into the product separation zone 130 in the liquid phase via the first stream 122. The product separation zone 130 can contain trays, baffles, packing, or other structure(s) configured to perform distillation of the second product olefin and any unreacted reactant olefin such that the second product olefin condenses to form the liquid portion described herein and the unreacted reactant olefin remains in vapor phase to form the vapor portion described herein. In aspects, the second product olefin and any unreacted reactant olefin are introduced to a top distillation tray of the product separation zone 130 of the distillation column 201, and the top distillation tray is below the liquid collection tray 203. The vapor portion moves in the direction of arrow 232 into the reaction zone 110 of the distillation column 201 via the vapor passage 204 that is formed in the liquid collection tray 203. The movement of vapor portion in direction of arrow 232 into the reaction zone 110 can be referred to as recycling the vapor portion from the product separation zone 130 to the reaction zone 110. Once in the reaction zone 110, at least a portion of the vapor portion can condense to enter the liquid phase and to react in the presence of the homogeneous metathesis catalyst system that is also contained in the liquid phase of the reaction zone 110 in the distillation column 201. The liquid portion moves in the direction of arrow 233, down the distillation column 201, exiting the distillation column 201 via stream 234. Stream 234 can contain a reboiler configured to heat and recycle at least a portion of the liquid portion to the product separation zone 130 in the distillation column 201, to provide heat to the distillation column 201 and to improve separation efficiency of the product separation zone 130 of the distillation column 201.

In aspects, a temperature and pressure at any point of the product separation zone 130 in the distillation column 201 are sufficient such that the second product olefin is recovered in the liquid portion and the unreacted reactant olefin is recovered in the vapor portion from the product separation zone 130.

The vapor phase containing the first product olefin and any unreacted reactant olefin can move into the second product separation zone 140 in the direction of arrow 212. The product separation zone 140 can contain trays, baffles, packing, or other structure(s) configured to perform distillation of the first product olefin and any unreacted reactant olefin such that the first product olefin remains in vapor phase to form the vapor portion described herein and the unreacted reactant olefin condenses to form the liquid portion that moves in the direction of arrow 244, down to the reaction zone 110. In aspects, the first product olefin and any unreacted reactant olefin moving in direction of arrow 212 can be introduced to a bottom distillation tray of the product separation zone 140 of the distillation column 201, and the bottom distillation tray is above the liquid collection tray 203 and above the reactive tray 202. The movement of liquid portion in direction of arrow 244 from the product separation zone 140 into the reaction zone 110 can be referred to as recycling the liquid portion from the product separation zone 140 to the reaction zone 110. Once in the reaction zone 110, at least a portion of the liquid portion can react in the presence of the homogeneous metathesis catalyst system that is also contained in the liquid phase of the reaction zone 110 in the distillation column 201. The vapor portion in the product separation zone 140 moves in the direction of arrow 212, up the distillation column 201, exiting the distillation column 201 via stream 242. Stream 242 can contain a condenser configured to condense and recycle at least a portion of the vapor portion in stream 242 to the product separation zone 140 of the distillation column 201, to improve separation efficiency of the product separation zone 140 of the distillation column 201.

In aspects, the temperature and pressure at any point in the product separation zone 140 of the distillation column 201 are sufficient such that the unreacted reactant olefin is recovered in the liquid portion and the first product olefin is recovered in the vapor portion from the product separation zone 140 of the distillation column 201.

In aspects, the pressures of the reaction zone 110, product separation zone 130, and product separation zone 140 in the distillation column 201 are about equal to one another.

FIG. 3 illustrates a schematic diagram of another apparatus 300 for performing an olefin metathesis process, where the reaction zone 110 and the second product separation zone 140 are in a distillation column 301 and the first product separation zone 130 is embodied with a stripping column 331. The second product separation zone 140 is above the reaction zone 110 in the distillation column 301. The second product separation zone 140 can also be referred to as a rectifying section of the distillation column 301.

The reaction zone 110 in distillation column 301 of the apparatus 300 is a space filled with liquid phase with or without reactive tray(s) above. The reactant olefin(s) and the homogeneous metathesis catalyst system are introduced via feed stream 10 into the distillation column 301 at a location that is above a top surface of the liquid phase or top reactive tray. Reaction components (e.g., the reactant olefin(s) and the homogeneous metathesis catalyst system) are introduced to the distillation column 301 and fall into the liquid phase in the reaction zone 110 of the distillation column 301.

Reaction effluent, also referred to herein as liquid phase, from the reaction zone 110 of apparatus 300, can flow in bottom stream 314 (stream 314 is equivalent of stream 114 in FIGS. 1A and 1B) to the catalyst separation zone 120. The bottom stream 314 is fluidly connected to the bottom of the distillation column 301 and to a catalyst separation unit of the catalyst separation zone 120. The catalyst separation unit in the catalyst separation zone 120 is configured, by a technique disclosed herein, to separate the liquid phase received via stream 314 into a first stream 122 containing the second product olefin and any unreacted reactant olefin and a second stream 124 containing the homogeneous metathesis catalyst system. First stream 122 is fluidly connected to the catalyst separation unit in the catalyst separation zone 120 and to the stripping column 331.

The second product olefin and any unreacted reactant olefin are received into the stripping column 331 in the liquid phase via the first stream 122. In aspects, the first stream 122 is connected to top of the stripping column 331 and is configured to introduce the second product olefin and any unreacted reactant olefin to a top of the stripping column 331 as liquid reflux. The stripping column 331 of the product separation zone 130 is configured to separate the second product olefin and any unreacted reactant olefin received via stream 122 into a vapor portion containing the unreacted reactant olefin and a liquid portion containing the second product olefin. The vapor and liquid portions move countercurrently within the stripping column 331. The vapor portion moves in stripping column 331 in the direction of arrow 337, and the liquid portion moves in the stripping column 331 in the direction of arrow 338. Because of mass transfer conditions in the stripping column 331, the unreacted reactant olefin received via stream 122 transfers from the liquid phase into the vapor portion, and the second product olefin received via stream 122 remains in liquid phase to form the liquid portion. In aspects, the stripping column 331 has a reboiler 335. In some aspects, the stripping column 331 can include a condenser, while in other aspects, the stripping column 331 does not include a condenser. That is, in some embodiments, the product separation zone 130 of apparatus 300 can include a condenser for stream 332 of the stripping column 331, while other aspects may not include a condenser for stream 332 of the stripping column 331. In aspects, the stripping column 331 can contain trays, baffles, packing, or other structure(s) configured to perform transfer of the unreacted reactant olefin into the vapor portion such that the second product olefin remains in liquid phase to form the liquid portion.

In aspects, the temperature and pressure at any point in the stripping column 331 are sufficient such that the second product olefin is recovered in the liquid portion and the unreacted reactant olefin is recovered in the vapor portion from the stripping column 331.

The processes 100A and 100B described herein, in context of the apparatus 300 of FIG. 3, can include receiving the vapor portion from the stripping column 331 into a reaction zone 110 of the distillation column 301 (e.g., via stream 332). FIG. 3 illustrates that the stream 332 is connected to a bottom of the distillation column 301; however, alternative aspects contemplate that the stream 332 can be connected to a side of the distillation column 301 that is fluidly connected to the reaction zone 110 in the distillation column 301 or to the product separation zone 140 in the distillation column 301.

The processes 100A and 100B described herein, in context of the apparatus 300 of FIG. 3, can also include removing the liquid portion from a bottom section of the stripping column 331. The liquid portion can be removed via stream 333 that is fluidly connected to the stripping column 331. The bottom section can be the bottom of the stripping column 331 (as illustrated in FIG. 3) or a side of the stripping column 331 that is near the bottom.

The processes 100A and 100B described herein, in context of the apparatus 300 of FIG. 3, can also include, after removing the liquid portion from the bottom section of the stripping column 331, reboiling at least a portion of the liquid portion. Stream 333 containing the liquid portion can be fluidly connected to the reboiler 335. In the reboiler, the liquid portion is heated, and at least a portion of the liquid portion can convert to vapor phase and flow in stream 336 back to the stripping column 331. Stream 336 can be connected to a side (as shown in FIG. 3) or to a bottom of the stripping column 331. The portion of the liquid portion that remains in liquid state can flow from the reboiler 335 via stream 334.

The flow of the vapor portion in stream 332 and into the reaction zone 110 of the distillation column 301 can be referred to as recycling the vapor portion from the product separation zone 130 to the reaction zone 110. Once in the reaction zone 110, at least a portion of the vapor portion can condense to enter the liquid phase and to react in the presence of the homogeneous metathesis catalyst system that is also contained in the liquid phase of the reaction zone 110 in the distillation column 301.

The vapor phase in the distillation column 301 that contains the first product olefin and any unreacted reactant olefin can move into the second product separation zone 140 of the distillation column 301 in the direction of arrow 312. The product separation zone 140 can contain trays, baffles, packing, or other structure(s) configured to perform distillation of the first product olefin and any unreacted reactant olefin such that the first product olefin remains in vapor phase to form the vapor portion described herein and the unreacted reactant olefin condenses to form the liquid portion that moves in the direction of arrow 344, down to the reaction zone 110 of the distillation column 301. In aspects, the first product olefin and any unreacted reactant olefin moving in direction of arrow 312 can be introduced to a bottom distillation tray of the product separation zone 140 of the distillation column 301, and the bottom distillation tray is above the liquid surface of the liquid phase in the reaction zone 110 of the distillation column 301. The movement of liquid portion in direction of arrow 344 from the product separation zone 140 into the reaction zone 110 can be referred to as recycling the liquid portion from the product separation zone 140 to the reaction zone 110. Once in the reaction zone 110, at least a portion of the liquid portion can react in the presence of the homogeneous metathesis catalyst system that is also contained in the liquid phase of the reaction zone 110 in the distillation column 301. The vapor portion in the product separation zone 140 moves in the direction of arrow 312, up the distillation column 301, exiting the distillation column 301 via stream 342.

In aspects, the temperature and pressure at any point in the product separation zone 140 of the distillation column 301 are sufficient such that the unreacted reactant olefin is recovered in the liquid portion and the first product olefin is recovered in the vapor portion from the product separation zone 140 of the distillation column 301.

In aspects, the pressures of the reaction zone 110 and product separation zone 140 in the distillation column 301 are about equal to one another.

Stream 342 can contain a condenser configured to condense and recycle at least a portion of the vapor portion in stream 342 to the product separation zone 140 of the distillation column 301, to improve separation efficiency of the product separation zone 140 of the distillation column 301.

Stream 334 can contain a reboiler configured to heat and recycle at least a portion of the liquid phase to the reaction zone 110 in the distillation column 301 or to the product separation zone 140 of the distillation column 301.

EXAMPLES

The following examples are illustrative of a metathesis reaction with reactant olefin(s) in liquid phase and in the presence of a homogeneous metathesis catalyst system.

Example 1 is a simulation of an olefin metathesis reaction with a homogeneous metathesis catalyst in a reaction zone 110 as disclosed herein. The reactant olefin was 1-butene, and the feed stream contained 100 wt % 1-butene. Double bond isomerization was set at 0.11 times the rate of metathesis. The simulation represented that ethylene and propylene flashed out of the reaction medium by distillation and did not react again. By choosing 1-butene conversion of 13.4% at steady state, the metathesis product contained 3.26 wt % ethylene, 0.14 wt % propylene, 86.59 wt % butene, 0.24 wt % pentene, and 9.77 wt % 1-hexene.

Example 2 is a simulation of an olefin metathesis reaction with a homogeneous metathesis catalyst in a reaction zone 110 as disclosed herein. The reactant olefin was 1-hexene, and the feed stream contained 100 wt % 1-hexene. Double bond isomerization was set at 0.11 times the rate of metathesis. The simulation represented that ethylene and propylene flashed out of the reaction medium by distillation and did not react again. By choosing 1-hexene conversion of 6.9% at steady state, the metathesis product contained 1.11 wt % ethylene, 0.03 wt % propylene, 0.04 wt % pentene, 93.11 wt % 1-hexene, 0.05 wt % heptane, 0.08 wt % nonene, and 5.58 wt % decene.

ADDITIONAL DESCRIPTION

Processes and apparatuses for olefin metathesis by reactive distillation have been described. The present application is also directed to the subject-matter described in the following numbered paragraphs (referred to as "para" or "paras"):

Para 1: A process for olefin metathesis by reactive distillation, comprising: reacting, in a reaction zone of a distillation column, a first reactant olefin in a presence of a homogeneous metathesis catalyst system to form a metathesis product comprising a first product olefin and a second product olefin.

Para 2: The process of Para 1, wherein the first product olefin has a carbon number that is less than a carbon number of the first reactant olefin, and wherein the second product olefin has a carbon number that is greater than the carbon number of the first reactant olefin.

Para 3: The process of Para 1 or 2, further comprising: (continuously) removing a liquid phase comprising the second product olefin and the homogeneous metathesis catalyst system from the reaction zone of the distillation column; and (continuously) removing a vapor phase comprising the first product olefin from the distillation column.

Para 4: The process of Para 3, further comprising: after removing the liquid phase, (continuously) separating the liquid phase into a first stream comprising the second product olefin and a second stream comprising the homogeneous metathesis catalyst system.

Para 5: The process of Para 3 or 4, wherein the liquid phase further comprises an unreacted reactant olefin comprising the first reactant olefin, wherein the first stream further comprises the unreacted reactant olefin, the process further comprising: (continuously) introducing the first stream into a first product separation zone; and (continuously) separating, in the first product separation zone, the second product olefin and the unreacted reactant olefin into a first vapor portion comprising the unreacted reactant olefin and a first liquid portion comprising the second product olefin.

Para 6: The process of Para 5, further comprising: recycling the first vapor portion to the reaction zone.

Para 7: The process of any of Paras 3 to 6, wherein the vapor phase further comprises the unreacted reactant olefin, the process further comprising: after removing the vapor phase, (continuously) introducing the vapor phase into a second product separation zone; and (continuously) separating, in the second product separation zone, the vapor phase into a second vapor portion comprising the first product olefin and a second liquid portion comprising the unreacted reactant olefin, wherein the second liquid portion flows from the second product separation zone to the reaction zone.

Para 8: The process of Para 7, wherein the reaction zone, the first product separation zone, and the second product separation zone are contained within the distillation column, wherein the first product separation zone is below the reaction zone, and wherein the second product separation zone is above the reaction zone.

Para 9: The process of any of Paras 1 to 8, wherein the reaction zone has a liquid collection tray positioned below a reactive tray in the distillation column, wherein the first reactant olefin and the homogeneous metathesis catalyst system are introduced into the distillation column above the reactive tray.

Para 10: The process of Para 9, wherein the liquid phase is removed from the reaction zone of the distillation column via a side draw stream that is fluidly connected to the liquid collection tray.

Para 11: The process of Para 9 or 10, wherein the first vapor portion is (continuously) recycled to the reaction zone via a vapor passage formed in the liquid collection tray.

Para 12: The process of Para 7, wherein the reaction zone and the second product separation zone are contained within the distillation column, wherein the second product separation zone is above the reaction zone in the distillation column, and wherein the first product separation zone is in a stripping column.

Para 13: The process of Para 12, wherein the first stream is (continuously) introduced to a top of the stripping column as reflux.

Para 14: The process of Para 12 or 13, further comprising: (continuously) receiving the first vapor portion from the stripping column into the reaction zone of the distillation column; (continuously) removing the first liquid portion from a bottom section of the stripping column; after removing the first liquid portion, (continuously) reboiling at least a portion of the first liquid portion; and introducing the at least a portion of the first liquid portion that is reboiled to the stripping column.

Para 15: The process of any of Paras 1 to 14, wherein the reaction zone does not include a heterogeneous metathesis catalyst.

Para 16: The process of any of Paras 1 to 15, wherein 1) one or more of the reactant olefin(s) is i) an alpha olefin, ii) a linear alpha olefin, iii) a normal alpha olefin, iv) or combinations thereof; 2) one or more of the product olefin(s) is i) an alpha olefin, ii) a linear alpha olefin, iii) a normal alpha olefin, iv) or combinations thereof; 3) the first product olefin is ethylene, propylene, or both ethylene and propylene; 4) the first product olefin has a carbon number that is less than the carbon number of the one or more reactant olefin(s); 5) the second product olefin has a carbon number that is greater than the carbon number of the one or more reactant olefin(s); 6) the reactant olefin(s) is 1-butene or 1-butene in combination with a higher carbon number olefin; 7) the reactant olefin(s) is 1-hexene or 1-hexene in combination with a higher carbon number olefin; 8) or combinations thereof.

Para 17: The process of any of Paras 1 to 16, wherein the homogeneous metathesis catalyst system comprises a metathesis catalyst dissolved in an inert solvent (e.g., toluene).

Para 18: The process of any of Paras 1 to 18, wherein the homogeneous metathesis catalyst system comprises a metal oxide based metathesis catalyst system, a metal halide based metathesis catalyst system, a metal carbene based metathesis catalyst system, or any combination thereof.

Para 19: The process of any of Paras 1 to 18, further comprising: (continuously) introducing a second reactant olefin to the reaction zone of the distillation column; and (continuously) reacting the second reactant olefin in the presence of the homogeneous metathesis catalyst system in the reaction zone to form the metathesis product.

Para 20: The process of Para 19, wherein the first product olefin has a carbon number that is less than a carbon number of the second reactant olefin, and the second product olefin has a carbon number that is greater than the carbon number of the second reactant olefin.

Para 21: The process of Para 19, wherein the first product olefin has a carbon number that is less than a carbon number of the second reactant olefin and the carbon number of the first reactant olefin, and the second product olefin has a carbon number that is greater than the carbon number of the second reactant olefin and the carbon number of the first reactant olefin.

Para 22: The process of any of Paras 1 to 21, further comprising: (continuously) introducing the first reactant olefin and the homogeneous metathesis catalyst system into the reaction zone of the distillation column.

Para 23: The process of any of Paras 1 to 22, wherein the first reactant olefin is introduced to the reaction zone of the distillation column separately from the homogeneous metathesis catalyst system.

Para 24: The process of any of Paras 1 to 23, wherein the first reactant olefin and the homogeneous metathesis catalyst system are introduced together to the reaction zone of the distillation column.

Para 25: The process of any of Paras 19 to 24, wherein the first reactant olefin is introduced to the reaction zone of the distillation column separately from the second reactant olefin.

Para 26: The process of any of Paras 19 to 25, wherein the first reactant olefin and the second reactant olefin are introduced together to the reaction zone of the distillation column.

Para 27: An olefin metathesis system comprising:
a distillation column having a reaction zone, a first product separation zone below the reaction zone, and a second product separation zone above the reaction zone, wherein the reaction zone is configured to contact a first reactant olefin in the presence of a homogeneous metathesis catalyst system to form a metathesis product comprising a first product olefin and a second product olefin, wherein the reaction zone has a reactive tray and a liquid collection tray below the reactive tray, wherein the first product separation zone has at least one distillation structure, wherein the first product separation zone is fluidly connected to the reaction zone via a vapor passage of the liquid collection tray;
a catalyst removal unit fluidly connected to the liquid collection tray of the reaction zone of the distillation column and configured to receive a liquid phase containing the second product olefin, unreacted reactant olefin, and the homogeneous metathesis catalyst system from the liquid collection tray and to separate the liquid phase into a first stream comprising the unreacted reactant olefin and the second product olefin and a second stream comprising the homogeneous metathesis catalyst system; and
wherein the first stream is connected to the catalyst removal unit and to the first product separation zone of the distillation column,
wherein the first product separation zone is configured to separate the unreacted reactant olefin and the second product olefin into vapor portion containing the unreacted reactant olefin and a liquid portion containing the second product olefin.

Para 28: The system of Para 27 having any function, any aspect, feature, additional component with corresponding function, aspect, or feature, or combinations thereof, as described herein.

Para 29: An olefin metathesis system comprising:
a distillation column having a reaction zone and a product separation zone above the reaction zone, wherein the reaction zone is configured to contact a first reactant olefin in the presence of a homogeneous metathesis catalyst system to form a metathesis product comprising a first product olefin and a second product olefin, wherein the reaction zone has a reactive tray and a liquid collection tray below the reactive tray, wherein the product separation zone has at least one distillation structure, wherein the product separation zone is configured to receive a vapor phase containing unreacted reactant olefin and first product olefin from the reaction zone;
a catalyst removal unit fluidly connected to reaction zone of the distillation column and configured to receive a liquid phase containing the second product olefin, unreacted reactant olefin, and the homogeneous metathesis catalyst system from the reaction zone of the distillation column and to separate the liquid phase into a first stream comprising the unreacted reactant olefin and the second product olefin and a second stream comprising the homogeneous metathesis catalyst system;
a stripping column fluidly connected to the first stream and configured to receive the first stream at a top of the stripping column as reflux and to separate the first stream into a vapor portion comprising the unreacted reactant olefin and a liquid portion comprising the second product olefin,
wherein the product separation zone is configured to separate the unreacted reactant olefin and the first product olefin into vapor portion containing the first product olefin and a liquid portion containing the unreacted reactant olefin.

Para 30: The system of Para 29 having any function, any aspect, feature, additional component with corresponding function, aspect, or feature, or combinations thereof, as described herein.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, processes and steps described in the specification. As one of ordinary skill in the art will readily appreciate from the disclosure, processes, machines, manufacture, compositions of matter, means, processes, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, processes, or steps.

What is claimed is:

1. A process for olefin metathesis by reactive distillation, comprising:
reacting, in a reaction zone of a distillation column, a first reactant olefin in a presence of a homogeneous metathesis catalyst system to form a metathesis product comprising a first product olefin a second product olefin; and removing a liquid phase comprising the second product olefin and the homogeneous metathesis catalyst system from the reaction zone of the distillation column;

wherein the reaction zone has a liquid collection tray positioned below a reactive tray in the distillation column, wherein the liquid phase is removed from the reaction zone of the distillation column via a side draw stream that is fluidly connected to the liquid collection tray.

2. The process of claim 1, wherein the first product olefin has a carbon number that is less than a carbon number of the first reactant olefin, and wherein the second product olefin has a carbon number that is greater than the carbon number of the first reactant olefin.

3. The process of claim 1, further comprising:
removing a vapor phase comprising the first product olefin from the reaction zone.

4. The process of claim 3, further comprising:
after removing the liquid phase, separating the liquid phase into a first stream comprising the second product olefin and a second stream comprising the homogeneous metathesis catalyst system.

5. The process of claim 4, wherein the liquid phase further comprises an unreacted reactant olefin comprising the first reactant olefin, wherein the first stream further comprises the unreacted reactant olefin, the process further comprising:
introducing the first stream into a first product separation zone; and
separating, in the first product separation zone, the second product olefin and the unreacted reactant olefin into a first vapor portion comprising the unreacted reactant olefin and a first liquid portion comprising the second product olefin.

6. The process of claim 5, further comprising:
recycling the first vapor portion to the reaction zone.

7. The process of claim 6, wherein the first vapor portion is recycled to the reaction zone via a vapor passage formed in the liquid collection tray.

8. The process of claim 5, wherein the vapor phase further comprises the unreacted reactant olefin, the process further comprising:
after removing the vapor phase, introducing the vapor phase into a second product separation zone; and
separating, in the second product separation zone, the vapor phase into a second vapor portion comprising the first product olefin and a second liquid portion comprising the unreacted reactant olefin,
wherein the second liquid portion flows from the second product separation zone to the reaction zone.

9. The process of claim 8, wherein the reaction zone, the first product separation zone, and the second product separation zone are contained within the distillation column, wherein the first product separation zone is below the reaction zone, and wherein the second product separation zone is above the reaction zone.

10. The process of claim 9, wherein the first reactant olefin and the homogeneous metathesis catalyst system are introduced into the distillation column above the reactive tray.

11. The process of claim 1, wherein the reaction zone does not include a heterogeneous metathesis catalyst.

12. The process of claim 1, wherein the first product olefin is ethylene or propylene.

13. The process of claim 1, wherein the homogeneous metathesis catalyst system comprises a metathesis catalyst dissolved in an inert solvent.

14. The process of claim 13, wherein the homogeneous metathesis catalyst system comprises a metal carbene based metathesis catalyst system.

15. The process of claim 1, further comprising:
introducing a second reactant olefin to the reaction zone of the distillation column; and
reacting the second reactant olefin in the presence of the homogeneous metathesis catalyst system in the reaction zone to form the metathesis product.

16. The process of claim 15, wherein the first product olefin has a carbon number that is less than a carbon number of the second reactant olefin, and the second product olefin has a carbon number that is greater than the carbon number of the second reactant olefin.

17. A process for olefin metathesis by reactive distillation, comprising:
reacting, in a reaction zone of a distillation column, a first reactant olefin in a presence of a homogeneous metathesis catalyst system to form a metathesis product comprising a first product olefin a second product olefin;
removing a liquid phase comprising the second product olefin and the homogeneous metathesis catalyst system from the reaction zone of the distillation column;
after removing the liquid phase, separating the liquid phase into a first stream comprising the second product olefin and a second stream comprising the homogeneous metathesis catalyst system;
introducing the first stream into a first product separation zone;
removing a vapor phase comprising the first product olefin and an unreacted reactant olefin from the reaction zone;
after removing the vapor phase, introducing the vapor phase into a second product separation zone; and
separating, in the second product separation zone, the vapor phase into a first vapor portion comprising the first product olefin and a first liquid portion comprising the unreacted reactant olefin,
wherein the reaction zone and the second product separation zone are contained within the distillation column,
wherein the second product separation zone is above the reaction zone in the distillation column, and wherein the first product separation zone is in a stripping column.

18. The process of claim 17, wherein the first stream is introduced to a top of the stripping column as reflux.

19. The process of claim 17, further comprising:
separating, in the first product separation zone, the second product olefin and the unreacted reactant olefin into a second vapor portion comprising the unreacted reactant olefin and a second liquid portion comprising the second product olefin;
receiving the second vapor portion from the stripping column into the reaction zone of the distillation column;
removing the second liquid portion from a bottom section of the stripping column;
after removing the second liquid portion, reboiling at least a portion of the second liquid portion; and
introducing the at least a portion of the second liquid portion that is reboiled to the stripping column.

20. The process of claim 17, wherein the first liquid portion flows from the second product separation zone to the reaction zone.

* * * * *